United States Patent [19]

Burrage

[11] Patent Number: 4,815,210

[45] Date of Patent: Mar. 28, 1989

[54] MEDICAL PILL BREAKER

[76] Inventor: Robert H. Burrage, 57 Stonewood Rd., York, Pa. 17402

[21] Appl. No.: 126,040

[22] Filed: Nov. 27, 1987

[51] Int. Cl.⁴ ............................................. B26B 17/00
[52] U.S. Cl. ......................................... 30/176; 7/126; 7/133
[58] Field of Search ................. 30/173, 175, 176, 186, 30/191; 7/130, 133, 126

[56] References Cited

U.S. PATENT DOCUMENTS

| 681,756 | 9/1901 | Toquet | 30/176 |
|---|---|---|---|
| 1,399,958 | 12/1921 | Gilbert | 30/186 |
| 1,800,317 | 4/1931 | Ries et al. | 30/176 |
| 1,814,014 | 7/1931 | Vitali | 7/132 |
| 1,840,044 | 1/1932 | Mattes | 30/186 X |
| 1,906,454 | 5/1933 | Elters | 81/3.44 |
| 1,994,532 | 3/1935 | Ratzlaff | 81/3.1 |
| 2,027,785 | 1/1936 | Rauh | 81/3.44 X |
| 2,070,217 | 2/1937 | Seger | 30/173 X |
| 2,729,125 | 1/1956 | Krzanowski | 7/126 X |
| 4,658,456 | 4/1987 | Tsai | 7/135 |

Primary Examiner—Frank T. Yost
Assistant Examiner—Eugenia A. Jones
Attorney, Agent, or Firm—C. Hercusjust

[57] ABSTRACT

A medical pill breaker comprising two complementary elongated members pivoted together intermediately of the opposite ends thereof, one end of the members being formed into at least a partial loop to comprise handles and opposite portions of the opposite ends of the members being concave and V-shaped in cross-section and comprising opposed members for breaking relatively lsrge pills, the opposite ends of the elongated members terminating in relatively shorter portions respectively V-shaped in cross-section and comprising breaking members for relatively smaller pills, and abutting portions on said elongated members comprising stop members to limit the closing of the V-shaped breaking members toward each other.

1 Claim, 1 Drawing Sheet

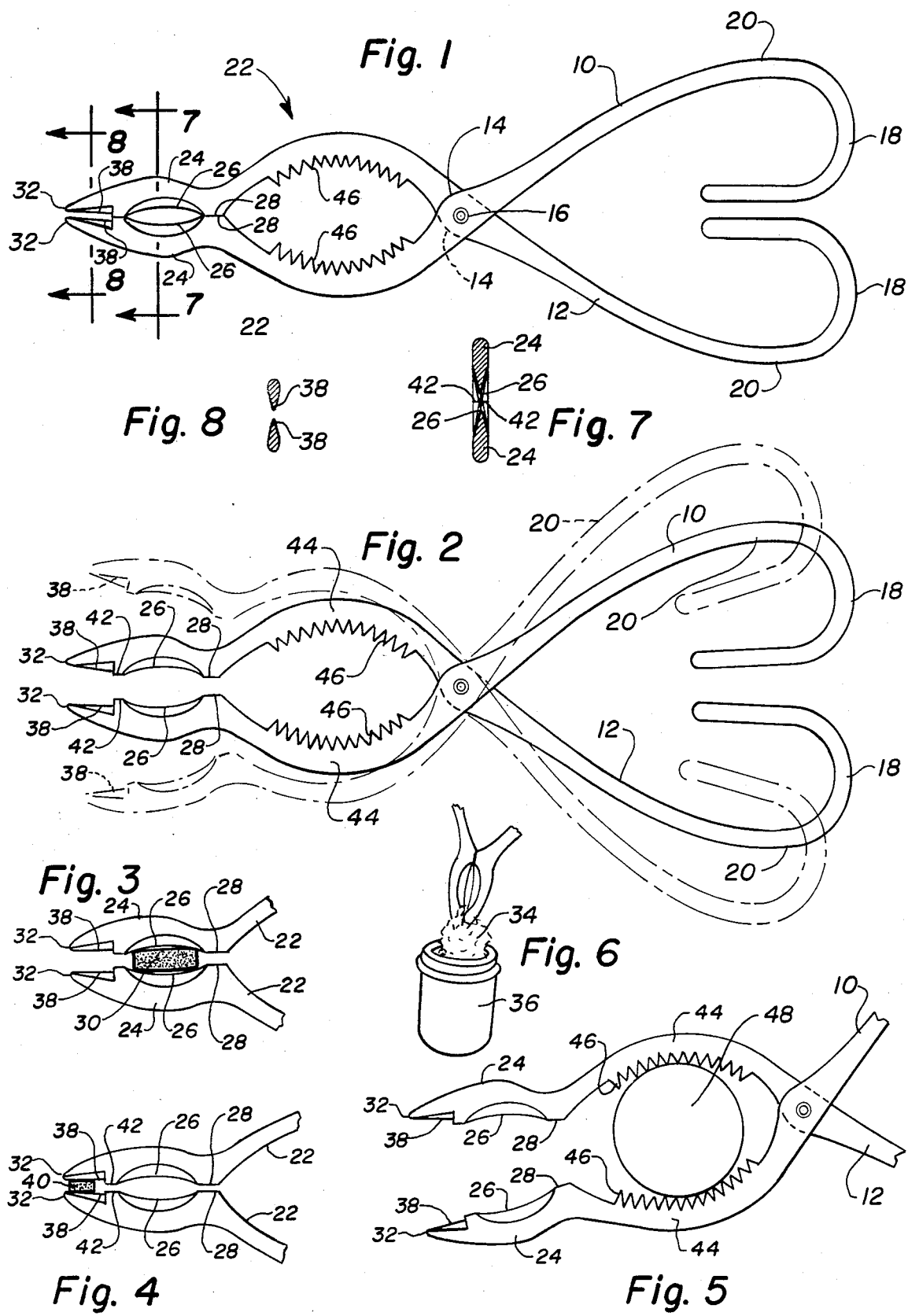

MEDICAL PILL BREAKER

BACKGROUND OF THE INVENTION

Aging population usually is accompanied with medication and especially the taking of various kinds of pills. In accordance with medical instructions, it sometimes is only necessary to take one-half or one-quarter of a pill. To facilitate this, various pill manufacturers form indented lines in pills to that they may be broken in half for half-dosage or in quarters for quarter-dosage. Often the pills are rather small and it is difficult to break them by hand. To offset this, a knife is sometimes employed to sever the pills but it is difficult to sever them evenly. The present invention has been developed to provide a simple but effective instrument designed to break pills with reasonable accuracy into halves or quarters or otherwise, as desired, and details thereof are set forth below.

SUMMARY OF THE INVENTION

It is the principal object of the present invention to provide a pill breaker, whether for medical or otherwise, comprising a pair of elongated members pivotally connected intermediately of the ends thereof and one end of each of said members is at least partially bent into a loop configuration to comprise handles. The opposite ends of the members respectively have concave portions facing each other and said portions, in cross-section, are V-shaped in order to comprise breaking members and the size thereof is sufficient to accommodate pills of relatively large size. Stop members are provided on the elongated members adjacent the opposite ends of the concave portions to limit the movement of said concave breaking members toward each other.

Another object of the invention is to render the breaking elements of the invention duplex in nature and comprising the aforementioned concave portions or sections and in addition, the terminal ends of said other ends of the pill breaker are sharply tapered and also in cross-section, have a V-shape to constitute breakers for pills of relatively smaller size than those accommodated in the concave breaking members but have blunt ends.

A further object of the invention is to taper the terminal ends of the opposite ends of said elongated members to facilitate insertion of the same in the neck of a pill bottle for purposes of grasping the cotton stuffing and removing it from the bottle, such removal frequently being difficult by the use of hands alone.

Still another object of the invention is to provide an additional concave section in each of the elongated members between the pivot and aforementioned concave breaking members, these portions of the pill breaker being larger than the concave breaking members and preferably are serrated for purposes of engaging caps on medicine bottles which frequently are screwed very tightly on the bottle and are difficult to remove manually. In this regard, the concave cutting members also may be employed to facilitate the cutting of sealing bands which frequently are applied to caps on medicine bottles, as well as on other bottles, and usually require a knife or some other similar instrument to effect removal but the concave breaking members eliminate the need for such additional instrument.

Still another object of the invention is to form the pair of elongated complementary members from metallic rod stock of suitable diameter, such as of the order of one-eighth inch or three-sixteenth inch diameter, without restriction thereto, and the portions of the members where they are pivoted is appropriately flattened to effect ready pivotal movement and further, the concave portions of the pivoted members readily are shaped in appropriate presses, and in addition, the V-shaped portions which comprise the breaking elements likewise may be formed by swaging or other means of pressure to distort the circular configuration into the desired V-shaped configuration.

Details of the foregoing objects and of the invention, as well as other objects thereof, are set forth in the following specification and illustrated in the accompanying drawing comprising a part thereof.

BRIEF DESCRIPTION OF THE DRAWING

FIG. 1 is a plan view of the preferred embodiment of the pill breaker comprising the invention and showing the pivoted member in so-called closed or breaking condition.

FIG. 2 is a view similar to FIG. 1 but shows, in full lines, one partially open condition of the breaker, while in phantom, a still further open position of the breaker is illustrated.

FIG. 3 is a view showing the concave breaking members in engagement with a relatively large pill which, upon further closing of the jaws, will effect breaking of the pill.

FIG. 4 is a view similar to FIG. 3 but shows a much smaller pill being engaged for breaking by the small, relatively straight V-shaped terminal ends of the breaking head of the instrument.

FIG. 5 is fragmentary illustration showing the relatively large concave sections of the elongated members engaging the cap of a pill bottle or the like to facilitate removal thereof.

FIG. 6 is a fragmentary vertical elevation showing the tip ends of the breaking jaws engaging a wad of cotton in an exemplary container to effect removal thereof.

FIG. 7 is a transverse sectional view, as seen on the line 7—7 of FIG. 1 and illustrating the V-shaped breaking portions, together with the stops which limit the movement thereof toward each other.

FIG. 8 is a transverse sectional view, as seen on the line 8—8 of FIG. 1 and illustrates in larger scale than employed in FIG. 1, the V-shaped configuration of the outermost breaking members of the instrument.

DETAILED DESCRIPTION OF THE PREFERRED EMBODIMENT OF THE INVENTION

Referring to FIGS. 1 and 2, it will be seen that the pill breaker comprising the invention is composed of a pair of complementary elongated members 10 and 12, which, intermediately of the ends thereof, have flattened portions 14 through which holes are drilled to accommodate a suitable rivet or screw 16 to secure the members 10 and 12 in ready pivotal connection. One end 18 of each of the members is at least partially formed into loops comprising handles 20.

The opposite end portions 22 of the elongated members 10 and 12 are provided with the breaking elements of the invention which in the preferred embodiment are duplex in nature. One relatively small arcuate portion 24 is shaped to provide opposed V-shaped breaking members 26. In the preferred construction of the pill breaker, preferably metallic rod stock of suitable diameter, such as of the order of one-eighth inch or three-sixteenth inch is selected which preferably is quite rigid and the arcuate concave members or elements 26 either may be formed by grinding or preferably by suitable pressure to effect swaging of the metal. Further, in order to limit the pivotal movement of the breaking members toward each other, each of the opposite ends 22 of the members 10 and 12 are provided with stop members or portions 28.

As shown in both FIGS. 1 and 3, and particularly FIG. 3, a pill 30 of relatively large size is disposed between the breaking members 26 and upon further closing of the members toward each other, breaking of the pill will be effected.

The relatively small arcuate portions 24 on the opposite ends 22 of members 10 and 12 terminate in relatively sharp, similar tapers, the outer ends 32 of which are blunt but can engage cotton 34, for example, in exemplary medical bottle 36 or the like. In addition, the outer ends 32 are provided with further relatively small and straight breaking members 38, which, are shown in FIG. 4, are utilized to engage and break a relatively small pill 40. Between the concave breaking members 26 and the relatively straight shorter breaking members 38, additional stop members 42 are provided as best shown and identified in FIG. 4.

Referring to FIG. 5, as well as being illustrated in FIGS. 1 and 2, there is an additional and substantially larger arcuate or concave section 44, the inner and oppositely-facing surfaces of which are provided with serrations 46, which are adapted to engage a cap 48 of a medicine bottle as shown in FIG. 5 to facilitate unscrewing the same from the neck of the bottle, not shown.

One further advantage of the present invention is that the larger breaking members 26 may be employed to engage sealing bands which frequently are heat-shrunk onto the caps and necks of bottles to prevent the possibility of atmosphere entering the bottle. The shape and sharpness of the breaking members 26 are adequate to sever such band by engaging the same and relatively rotating the pill breaker and the bottle.

From the foregoing, it will be seen that the present invention provides a relatively simple and effective pill breaker capable of being manufactured inexpensively and satisfies a long felt need in the pill industry. The complementary elements from which the handles are formed, together with the opposed concave portions of various sizes all are capable of being manufactured by means of dies from readily obtainable wire-like metallic rod stock of appropriate diameter. The V-shaped breaking elements likewise readily are formable by swaging or heavy pressure in a die and stop members are provided to limit the closing movements of the arcuate portions toward each other. The terminal ends 32 of the straight pill breakers 38 are blunt for safety purposes and are highly useful to engage cotton in the neck of a pill bottle, thereby further increasing the utility of the overall pill breaker.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

I claim:

1. A medical pill breaker comprising two complementary elongated members pivotally connected intermediately of the opposite ends thereof, one end of each member comprising a handle and the opposite ends having duplex pill-breaking portions which are in longitudinal alignment, the portions nearest the pivot comprising opposing concave arcuate faces which are symmetrically V-shaped in cross-section and comprise pill-breaking portions extending toward each other and respectively engageable with opposite faces of a pill when disposed between said concave arcuate breaking portions and said handles are moved toward each other, the other pill-breaking portions being substantially straight and shorter than said concave arcuate faces and are also symmetrically V-shaped in cross-section and are adapted to break pills which are smaller than those to be broken by said arcuate pill-breaking portions, said arcuate faces adjacent one end thereof also having abutment stops engageable to prevent said arcuate faces from crushing a pill and are also operable to abut each other prior to said shorter straight breaking portions meeting each other whereby they are spaced when said stops abut and prevent crushing said smaller pills and the terminal ends of said shorter straight pill-breaking portions are tapered and blunt for safety and are adapted to be inserted into cotton in a pill bottle to grip the same for removal from the bottle.

* * * * *